United States Patent [19]
Woyski et al.

[11] Patent Number: 5,665,919
[45] Date of Patent: Sep. 9, 1997

[54] HIGH FREQUENCY VIBRATION TEST FIXTURE WITH HYDRAULIC SERVO VALVE AND PISTON ACTUATOR

[75] Inventors: William B. Woyski, La Habra Heights; Robert C. Tauscher, Hacienda Heights, both of Calif.; Klaus L. Cappel, Madison, Ala.

[73] Assignee: Team Corporation, Burlington, Wash.

[21] Appl. No.: 594,473

[22] Filed: Jan. 31, 1996

Related U.S. Application Data

[60] Continuation of Ser. No. 248,372, May 24, 1994, abandoned, which is a division of Ser. No. 871,678, Apr. 20, 1992, Pat. No. 5,343,752.

[51] Int. Cl.$^6$ .................................................. G01M 7/06
[52] U.S. Cl. ......................................................... 73/665
[58] Field of Search ........................... 73/663, 665, 668; 137/625.63, 625.6

[56] References Cited

U.S. PATENT DOCUMENTS

| | | | |
|---|---|---|---|
| 4,011,749 | 3/1977 | Cappel | 73/71.6 |
| 4,145,956 | 3/1979 | Rumrill, Jr. et al. | 137/625.64 |
| 4,293,002 | 10/1981 | Moriyama et al. | 137/625.64 |
| 4,403,511 | 9/1983 | Shibano et al. | 73/665 |
| 4,506,758 | 3/1985 | Fair | 73/665 |
| 4,576,203 | 3/1986 | Boyer et al. | 137/625.63 |
| 4,593,719 | 6/1986 | Leonard | 137/625.63 |
| 4,741,364 | 5/1988 | Stoss et al. | 137/625.64 |
| 4,748,851 | 6/1988 | Yoneda | 73/668 |
| 4,875,501 | 10/1989 | Ichihashi et al. | 137/625.64 |
| 4,996,881 | 3/1991 | Tauscher et al. | 73/663 |

FOREIGN PATENT DOCUMENTS

| | | | |
|---|---|---|---|
| 0011335 | 2/1981 | Japan | 73/663 |
| 0028837 | 2/1986 | Japan | 73/663 |

OTHER PUBLICATIONS

"Proposal 15351," Dec. 4, 1990 pp. 13–14.
*Hydrashakers,* Team Corporation Catalog, pp. 1–16.

*Primary Examiner*—Hezron E. Williams
*Assistant Examiner*—Nashmiya Ashraf
*Attorney, Agent, or Firm*—Christie, Parker & Hale LLP

[57] ABSTRACT

A vibration test fixture includes a reciprocating slip plate carrying an article subjected to vibration and shock testing. A pair of opposed, spaced apart low oil pressure hydrostatic linear bearings support the slip plate during reciprocating single-axis linear travel on the bearings. The slip plate is mounted to each bearing by a single-axis bearing guide system confining the slip plate to reciprocating longitudinal travel on generally planar, two-dimensional bearing surfaces that support the load of the slip plate. The slip plate is reciprocated by a voice coil-driven hydraulic servo valve and double-acting piston actuator integrated into the vibration table between the bearings that support the slip plate. The voice coil connects directly to a pilot valve in the servo valve assembly. The voice coil generates a vibrating linear motion input that reciprocates the pilot valve at controlled frequencies to induce alternating hydraulic fluid flow control outputs from the servo valve for reciprocating the actuator pistons that drive the slip plate. Other embodiments include a multiple-axis, multiple degree-of-freedom vibration test fixture, and a multiple stage hydraulic servo valve that can be integrated into a piston drive system to achieve high frequency and high force levels in a hydraulic vibration test fixture. Combined large acceleration forces up to about 6 g's at high frequencies up to about 2000 Hz can be produced in one embodiment of the invention.

9 Claims, 10 Drawing Sheets

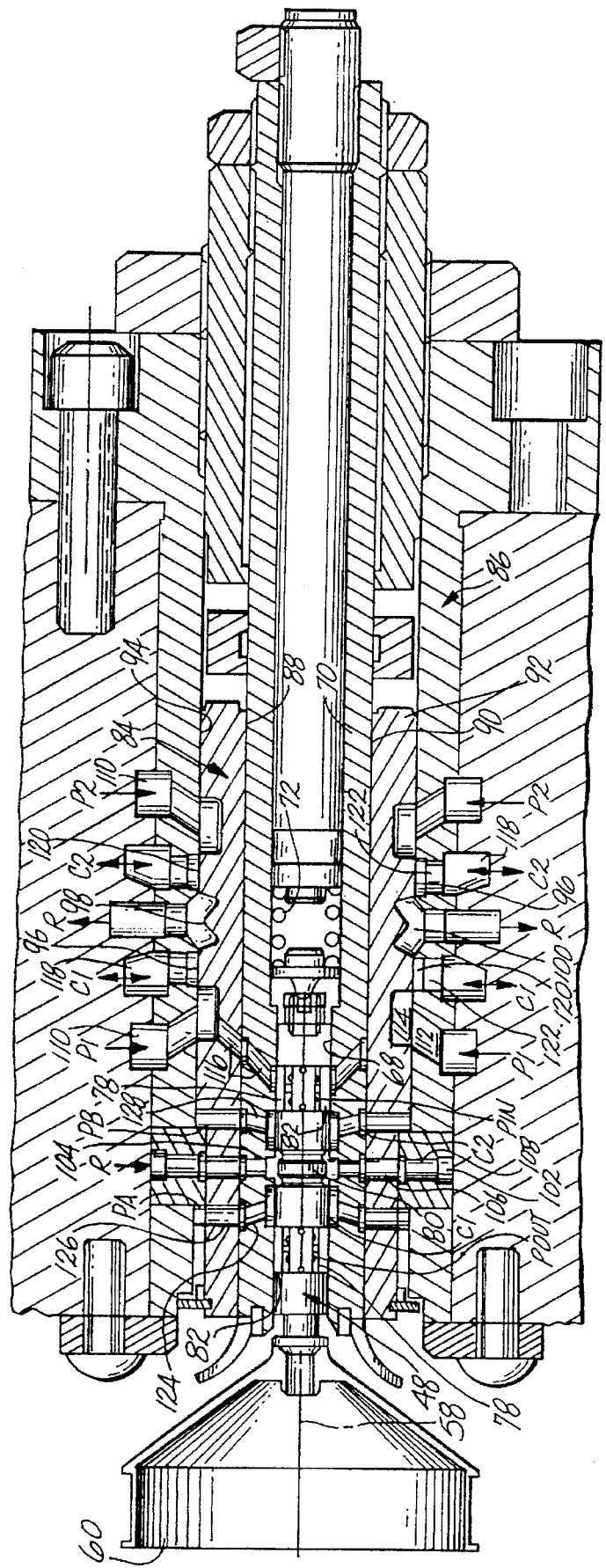

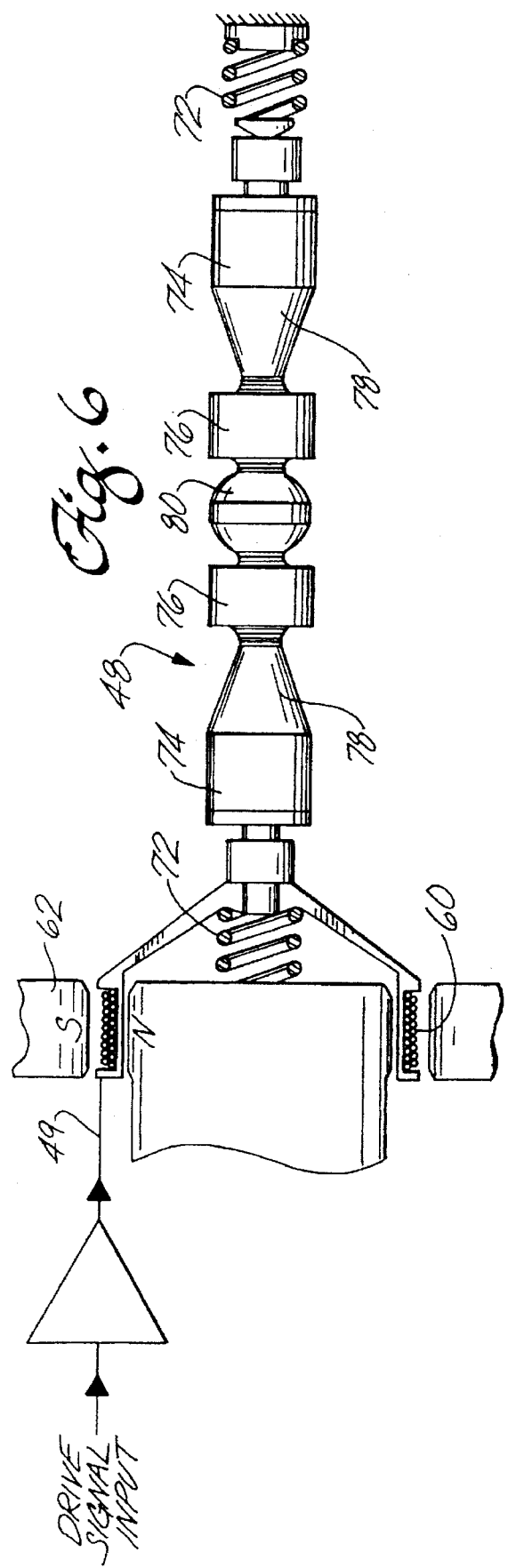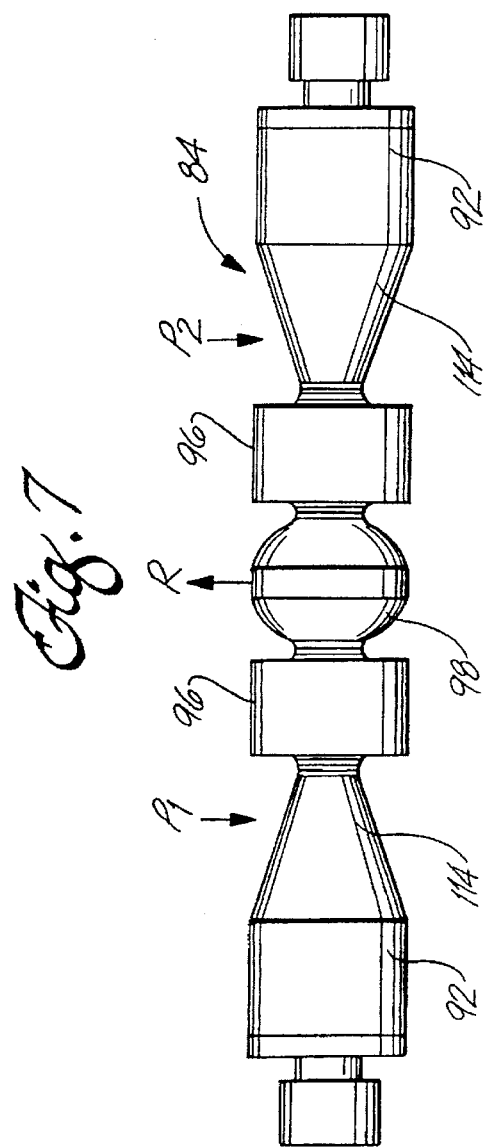

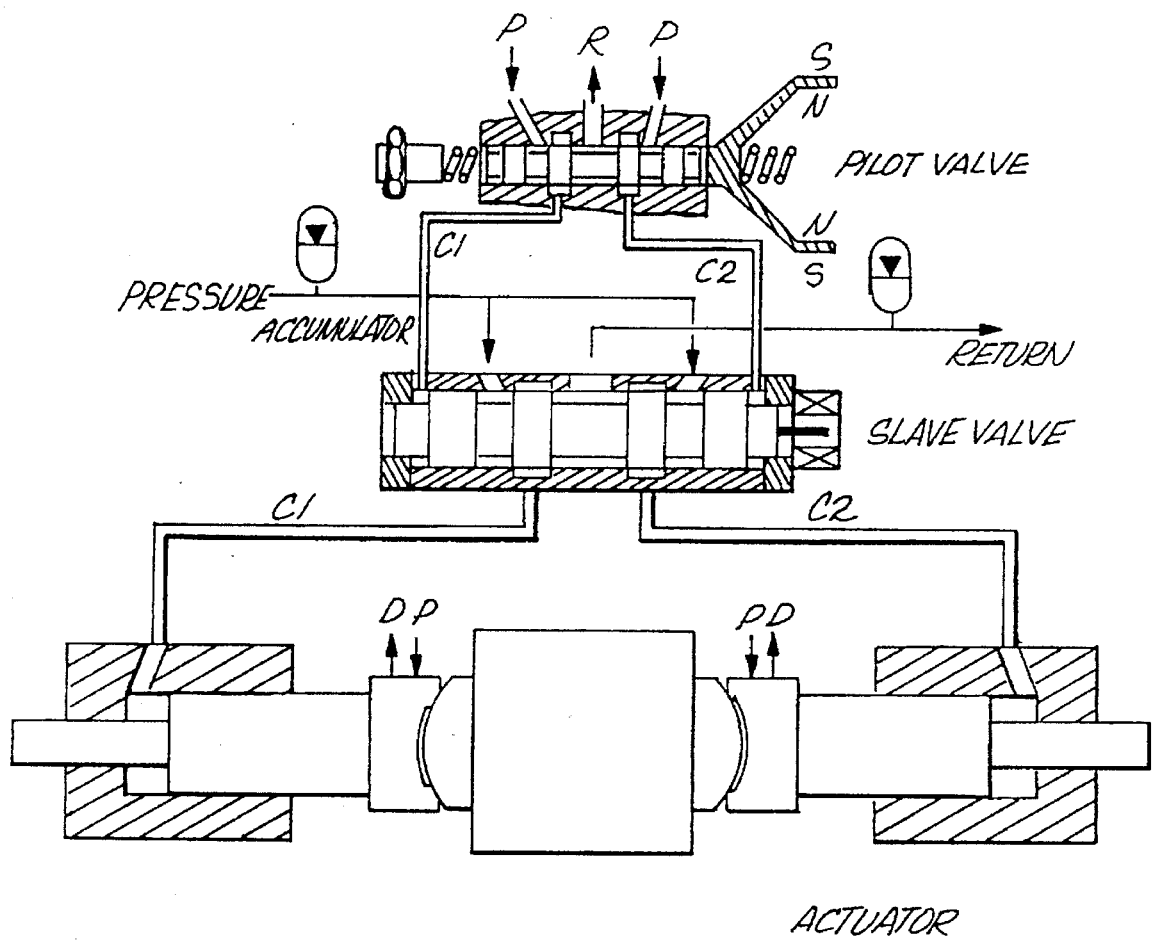

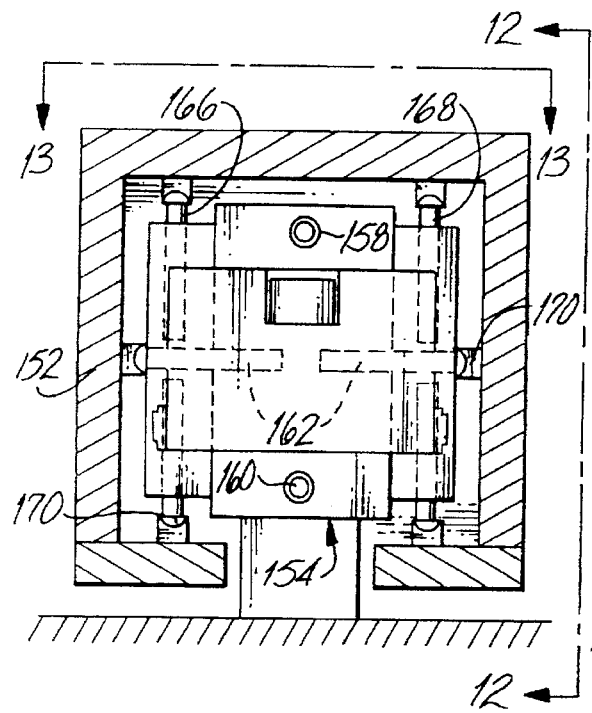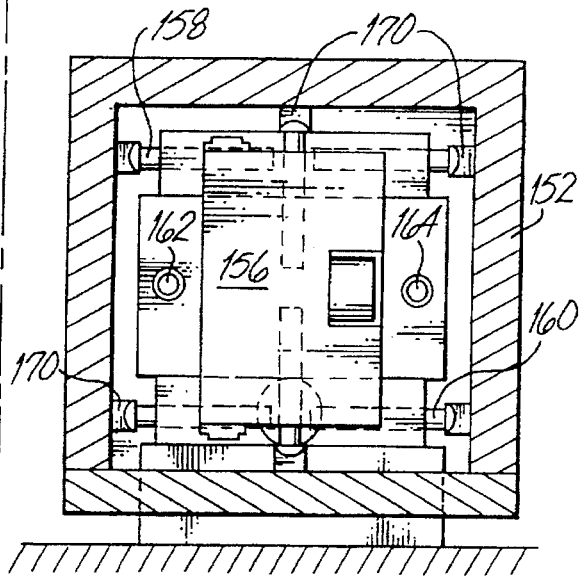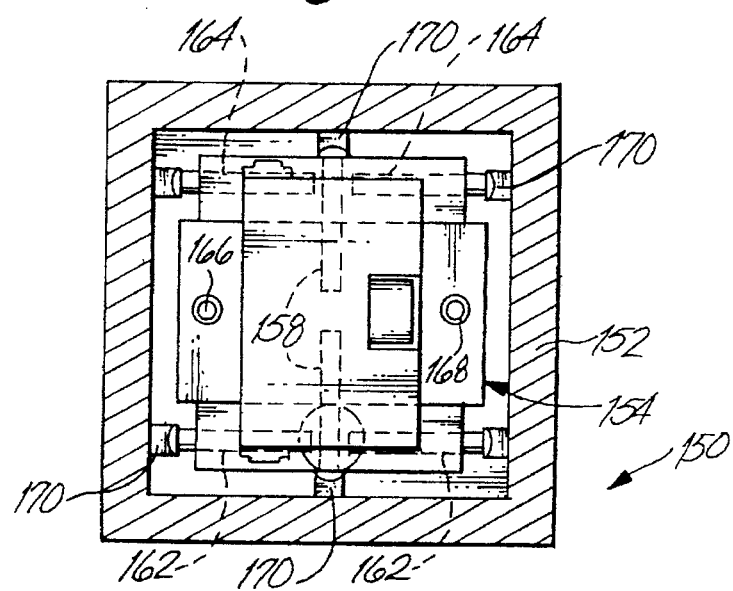

HIGH FREQUENCY VIBRATION TEST FIXTURE WITH HYDRAULIC SERVO VALVE AND PISTON ACTUATOR

CROSS-REFERENCE TO RELATED APPLICATION

This application is a continuation of Ser. No. 08/248,372, filed May 24, 1994, now abandoned, which is a division of Ser. No. 07/871,678, filed Apr. 20, 1992, now U.S. Pat. No. 5,343,752.

FIELD OF THE INVENTION

This invention relates to vibration testing equipment for simulating vibration and shock loads on an article under test, and more particularly, to a vibration table driven by a hydraulic servo valve-controlled piston actuator for vibrating the table at high frequencies and/or high force levels. Embodiments of the invention include a double-acting piston actuator with an integrated servo valve controller for a hydraulic vibration test table, and multiple-axis, multiple degree-of-freedom vibration test fixtures.

BACKGROUND OF THE INVENTION

The vibration test industry, including all major aerospace firms, automotive manufacturers, electronics companies, and the like, has adopted use of various methods and systems to simulate vibration and shock environments for determining their products' effectiveness and longevity when subjected to these environmental extremes. Vibration testing is often used to develop vibration-tolerant designs; some use it to verify that a product will survive in its intended vibrating environment; others use it to screen out defective parts at an early stage in the manufacturing process. For instance, vibration and shock testing often involves the testing of electronic circuit boards adapted for use in spacecraft, airplanes, automobiles, etc. The boards are subjected to vibration testing, often at high frequencies, or high force levels, to determine whether or not they will survive the shaking required when the hardware is placed in use.

In the past, test fixtures in the form of "vibration tables" have been used for producing vibration and shock loads on an article under test. These vibration tables (which are also referred to as oil film tables, slip tables, or bearing tables) include a horizontal or vertical table on which the test article is mounted. The table is vibrated at a desired frequency, force level, and/or amplitude during testing. One such vibration test fixture is manufactured and sold under the name T-Film Table by Team Corporation, South El Monte, Calif. the assignee of this application. This vibration test fixture is disclosed in U.S. Pat. No. 4,996,881, incorporated herein by this reference.

Vibration testing has traditionally been done with the test article restrained to move in a single axis. Recent studies show, however, that vibration testing in three mutually exclusive axes simultaneously can simulate real world conditions better than single axis testing. The present invention, in one embodiment, comprises a vibration test fixture adapted for single axis vibration; other embodiments of the invention comprise multiple-axis, multiple-degree-of-freedom vibration test fixtures.

Vibration frequency is selected to maximize the effectiveness of the testing. Transportation tests, for example, require frequencies from about 2 to about 500 Hz to simulate truck, rail or air transportation vibration. Screening and qualification tests may require that the frequency of vibration extend up to about 2,000 Hz for testing components with high natural frequencies. The vibration test generation and control input may be specified to be either sinusoidal motion, random motion, or to duplicate measured real-time waveforms. Vibration testing also can be applied at different force levels to meet certain maximum acceleration specifications.

The different types of test equipment currently available to produce vibration motion for a test article have limitations that require improvements. Electrodynamic shakers make up the largest percentage of purchased vibration force generators. They produce frequency response up to approximately 2,000 Hz and force ranges from about one pound to approximately 50,000 pounds. However, they are extremely expensive; they have relatively small specimen mounting areas; and they must often use a "head expander," a fixture that increases the mounting area for testing in the vertical axis, or a slip table or hydrostatic bearing system for testing in the horizontal axis. The electrodynamic shaker system adds considerable size to the usable specimen mounting surface, often taking up more room on the laboratory or production floor than is needed for the test object alone.

Hydraulic shakers have proved to be a viable alternative (compared with electrodynamic shakers) for all vibration testing, except those tests that require high frequency responses above about 500 to 1,000 Hz. Hydraulic shakers are physically much smaller than electrodynamic shakers, since the conversion of hydraulic power to vibrating motion can be accomplished with a much smaller mechanism. Hydraulic shakers also are much less expensive.

Head expanders, being physical devices, respond to certain driving frequencies by resonating. At each resonant frequency, the head expander deforms into a characteristic shape, and the frequency and shape together define that mode of vibration. The effect of the modes is to make the vibrating motion on the mounting surface of the head expander nonuniform. At a modal frequency, one location on the mounting surface may move less than the shaker input, while a different location may be moved more than is desired. Head expanders also add mass to the vibration test system, requiring much more force of the shaker than the test article alone.

A slip plate, and more precisely, the moving element of any horizontal vibration test fixture, has modes of vibration and suffers from the same deficiencies as head expanders. In addition to normal modes, the slip plate and shaker system is often long enough so that pressure or stress wave phenomena are observed to significantly degrade the uniformity of vibration of the slip plate surface. The observed phenomenon is that, when controlling the amplitude of a vibration test by monitoring the end of the slip plate, the front and center of the slip plate are often seen to have much lower amplitude over a wider range of frequencies. Conversely, if the test is controlled by monitoring the front of the slip plate, then the end is observed to have much higher amplitudes than desired.

These physical phenomena reduce the useful area of a head expander or a slip plate because it is not possible to obtain uniform vibration input over the entire surface.

The present invention provides a hydraulic vibration test fixture that overcomes the disadvantages of prior art electrodynamic shakers and hydraulic shakers. The test fixture avoids the cost and the space requirements and limitations of electrodynamic actuators, while achieving the higher frequency and load level capabilities normally associated only with electrodynamic shakers and not achieved by prior art hydraulic vibration test fixtures. Greatly improved uniformity of vibration amplitude across the useful surface area of the vibration table also is produced. Improvements in multiple-axis, multiple degree-of-freedom shakers are also provided.

SUMMARY OF THE INVENTION

Briefly, one embodiment of the invention comprises a vibration test fixture having a fixture base for carrying a unit under test, and a hydraulic vibration actuator having a cylinder, a piston that reciprocates in a bore within the cylinder, and a reciprocating piston rod extending from the piston to the outside of the cylinder. The vibration actuator is mounted to the fixture base to transfer reciprocating motion of the piston rod into vibrational motion of the fixture base for vibration testing of the unit under test. The piston has an end face, opposite from the piston rod, exposed to a trapped volume of hydraulic fluid contained within a space in the bore adjacent the end face of the piston. An inlet port in the cylinder leads to the trapped hydraulic fluid contained adjacent the end face of the piston. A hydraulic servo valve adjacent the cylinder has an alternating waveform input that induces the servo valve to produce a hydraulic fluid flow control output at a frequency corresponding to the desired frequency of vibration of the unit under test. The hydraulic fluid flow output from the servo valve is in close proximity to and passes directly into the inlet port leading to the piston cylinder. Fluid flow from the servo valve output to the cylinder inlet port is over as short a distance as possible, preferably via a passage of essentially negligible length. This minimizes the volume of compressible fluid trapped between the servo valve output and the piston. This minimized volume of hydraulic fluid between the servo valve and the piston improves hydraulic stiffness, thereby increasing the natural frequency of the system. One factor that has limited the frequency response of a hydraulic shaker is the compressibility of the hydraulic fluid. Flow rate required to achieve frequencies of vibration greatly in excess of the natural frequency increases proportional to frequency. That is, a certain amount of additional hydraulic fluid flow within the drive system is required to compress the fluid before vibration motion is initiated.

A further embodiment of the invention includes a vibration actuator having a double-acting piston with separate minimized trapped volumes of hydraulic fluid adjacent corresponding end faces of the pistons. A hydraulic servo valve can be integrated into the double-acting pistons so that fluid flow outputs from the servo valve are in close proximity to the trapped volumes of fluid adjacent the pistons. The trapped volumes of fluid between the servo valve outputs and the input ports to the piston cylinders are sufficiently minimized to produce high frequency responses, in one embodiment on the order of 1,000 to 2,000 Hz. This high frequency response is possible with good levels of output force.

A further embodiment of the invention comprises a servo valve for a hydraulic vibration test fixture. The servo valve has a pilot valve stage in which a pilot valve reciprocates at high frequencies in response to a vibrating mechanical frequency input. The servo valve also includes a slave valve stage concentric with and surrounding the pilot valve stage that amplifies the power output of the servo valve while minimizing the trapped volume of hydraulic fluid between the two stages of the servo valve. This results in good power output at high frequencies. By integrating this servo valve into the piston actuator, the trapped volume of fluid between the pilot valve stage of the servo valve and the end face of the adjacent piston is minimized. In addition, the larger effective area of the slave valve stage spool generates a sufficiently high valve flow necessary to achieve high levels of high frequency response.

Another embodiment of the invention comprises a hydraulic vibration test fixture having a slip plate adapted for carrying an article subjected to shock or vibration testing. Spaced-apart bearings support the slip plate for reciprocating sliding motion along a common longitudinal axis of travel. Each bearing includes a corresponding bearing guide member affixed to the slip plate for guiding the reciprocating sliding travel of the slip plate. A drive actuator for inducing vibrating motion to the slip plate is integrated into the test fixture bearing system. The actuator is preferably the type of piston actuator described previously, and includes a housing disposed between the spaced-apart bearings, with opposed reciprocating drive members (piston rods) extending from opposite sides of the actuator housing. The actuator drive members are affixed to corresponding guide members on the adjacent bearings. The drive actuator further includes a hydraulic servo valve controller integrated into the actuator housing between the drive members. Vibration motion produced in the drive members by the servo valve is preferably from the type of concentric pilot-stage/slave-stage servo valve described previously. This induced vibrating motion of the drive members causes corresponding reciprocating forces on the bearing guide members to vibrate the slip plate. The slip plate is therefore driven directly by drive forces originating from within the hydraulic servo valve-controlled actuator that is integrated into the bearing support and guide system of the test fixture table. This arrangement not only produces high frequency responses in a hydraulic vibration test fixture, but also achieves a greater uniformity of vibration forces spread out over the active surface area of the slip plate.

In one embodiment of the actuator drive, the hydraulic servo valve input can be from a voice coil or other transducer directly coupled to the pilot valve for reciprocating the pilot valve at controlled frequencies. The alternating hydraulic fluid flow control outputs from the servo valve are produced in response to the reciprocating motion of the pilot valve induced by the voice coil. The actuator drive members comprise hydraulically driven pistons extending from opposite sides of the actuator housing, and the servo valve is integrated into the housing between the pistons. Since the voice coil, servo valve and piston actuators are all integrated into a single modular drive unit, the hydraulic fluid flow outputs from the voice coil-controlled servo valve can be directed toward adjacent end faces of the pistons in a system that minimizes the amount of trapped hydraulic fluid between the pilot valve and the pistons. This arrangement minimizes space requirements and makes the invention especially applicable to modular actuator-driven, multiple-axis, multiple degree-of-freedom vibration test fixtures.

Another embodiment of the invention comprises a multiple-axis vibration test fixture comprising a fixture base for carrying a unit under test, and a plurality of separate vibration actuators affixed to the base. Each of the vibration actuators preferably comprises the modular actuator-servo valve unit described previously. Each vibration actuator includes an actuating arm that reciprocates along an exclusive axis aligned at an angle with respect to and intersecting the axes of other similar vibration actuators. The vibration actuators apply a vibrating motion to the fixture base along their corresponding axes to vibrate the fixture base in multiple axes. Means are provided for decoupling from each vibration actuator the motion imparted to the fixture base from the other vibration actuators. The forces from other vibration actuators are decoupled from each actuator preferably by spherical bearing ends of the piston rods which are slidable and rotatable with respect to corresponding spherical bearing supports affixed to the fixture base. By providing such freedom of sliding and rotating motion with respect to the force-applying ends of each vibration actuator, the modular vibration actuator units can be mounted to a fixture base to apply vibration forces in multiple directions in many different configurations of multiple axis, multiple degree-of-freedom vibration test fixtures.

The vibration test fixture provided by the integrated actuator drive system provides substantial improvements over the conventional vibration testing apparatus described previously. These improvements include less space required, easier access around the vibration test table, higher frequency response, reasonably uniform vibration levels over the entire useful surface area of the vibration table, reduced cost, and greatly reduced oil leakage problems. The objective of obtaining high frequency responses in the range from about 1,000 Hz to about 2,000 Hz in a hydraulic shaker is achieved by the system minimizing the trapped volume of compressible fluid between the piston and valve, in combination with producing the high valve flow rate necessary to operate with compressible flow at such high frequencies.

In addition, the invention enhances modular design of vibration tables and their drive systems. The use of multiple actuator drive system modules, for instance, can produce a corresponding increase in actuator force when large single axis g-forces are required. The modular design of the actuator drive system also provides test fixtures for vibration testing in mutually exclusive axes, in addition to single-axis vibration testing.

These and other aspects of the invention will be more fully understood by referring to the following detailed description and the accompanying drawings.

BRIEF DESCRIPTION OF THE DRAWINGS

FIG. 5 is a cross-sectional view illustrating components of the servo valve.

FIG. 6 is a semi-schematic view showing a voice coil and pilot valve component of the servo valve.

FIG. 7 is a semi-schematic view showing a slave valve spool component of the servo valve.

FIG. 8 is a schematic view of a prior art vibration actuator and servo valve system described in the Example set forth in the detailed description.

FIG. 11 is a semi-schematic front elevation view showing an alternative embodiment of a multiple-axis, multiple degree-of-freedom vibration test module.

FIG. 12 is a semi-schematic side elevation taken on line 12—12 of FIG. 11.

FIG. 13 is a semi-schematic top view taken on line 13—13 of FIG. 11.

DETAILED DESCRIPTION

Figure 1:
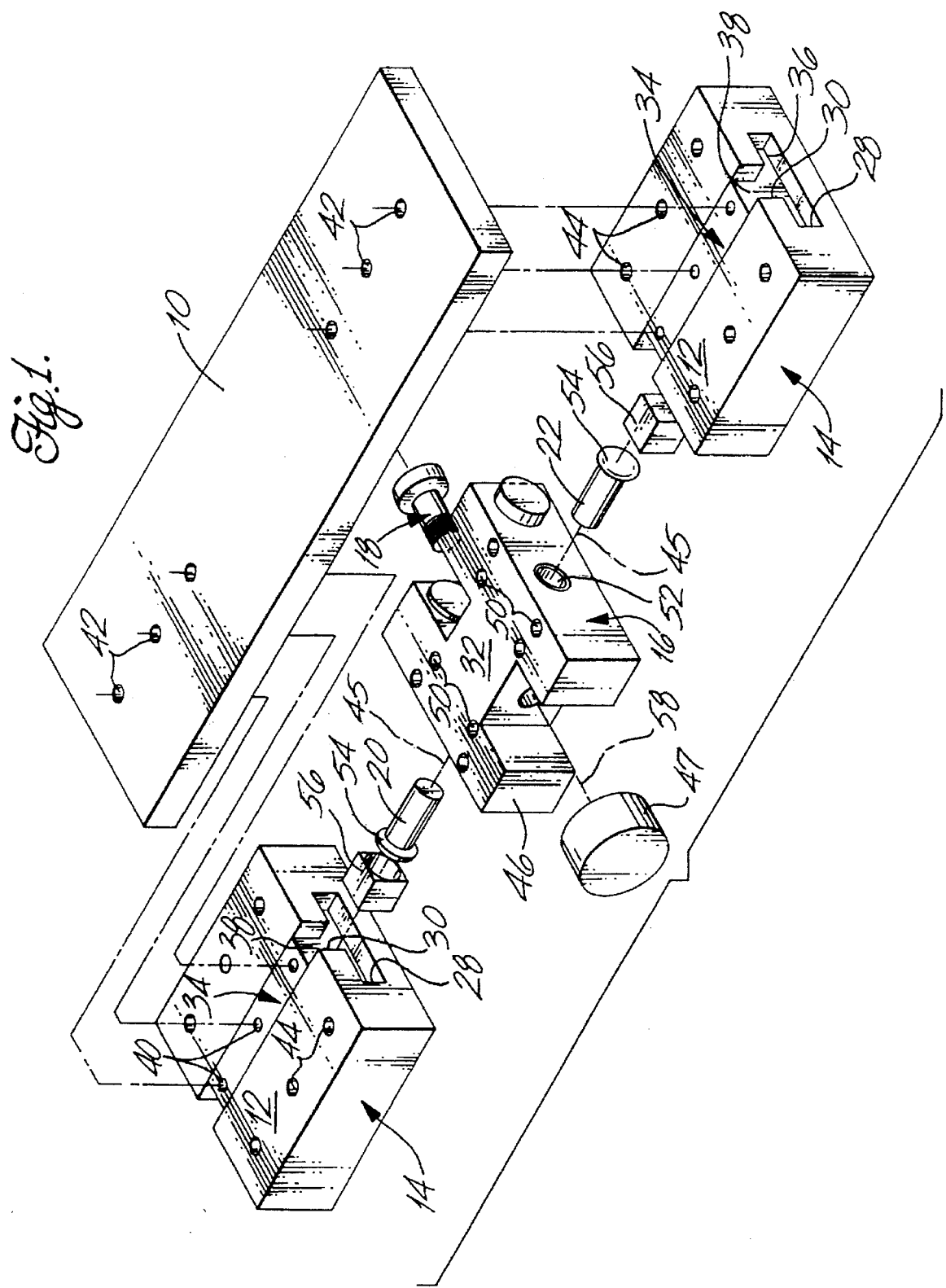
FIG. 1 is an exploded semi-schematic perspective view illustrating components of a vibration test fixture according to principles of this invention.

FIG. 1 is an exploded perspective view showing principal components of a vibration test fixture which illustrates one embodiment of the inventions. FIGS. 2 through 7 are more detailed views of a specific embodiment of the invention shown generally in FIG. 1. The fixture shown in FIGS. 1 through 7 is one embodiment of the invention incorporated into a hydraulic shaker table vibrated along a single horizontal axis for vibration and shock testing of an article affixed to the table. This embodiment is for the purpose of illustrating one use of the invention; other uses also are possible, such as in vertical axis shakers or multiple-axis shaker tables. FIG. 1 also illustrates a single hydraulic drive actuator unit for applying vibration forces along a single axis of the table, but this is simply one embodiment to illustrate principles of the invention. Multiple drive systems of similar design can be used on multiple parallel drive axes or on multiple exclusive axes for vibrating the table.

In addition, the invention is illustrated in FIGS. 1 through 7 with respect to a single axis horizontal shaker table, preferably of the type manufactured by Team Corporation, and sold under the name T-Film Table. As mentioned previously, this type of vibration test fixture is described in U.S. Pat. No. 4,996,881. The invention can, however, be used in other types of vibration tables.

To briefly describe the type of shaker table with which the invention is used, as illustrated in FIG. 1, the test fixture includes a rigid and generally planar slip plate 10 mounted for reciprocating linear travel on flat upper bearing surfaces 12 of a pair of longitudinally spaced apart support bearings 14. The slip plate 10 is of generally uniform thickness and has a generally rectangular surface area within a region of its bottom surface that is supported for linear travel on the upper bearing surfaces 12. Recessed regions (shown at 51 in FIG. 2) are located in the top surfaces of the bearings 14. These recessed regions are used to supply lubricating oil under low pressure to the bottom surface of the slip plate and to the tops of the bearings for lubricating sliding travel of the slip plate 10 back and forth on the upper bearing surfaces 12 during vibration testing.

According to principles of the invention, the vibration table is driven by a hydraulic actuator drive unit 16 having a double-acting hydraulic drive piston actuator controlled by a hydraulic servo valve 18. The actuator drive unit 16 is disposed between the pair of axially aligned and spaced-apart guide bearings 14 that support the shaker table 10 for its linear reciprocating travel. The actuator drive unit includes pistons 20 and 22 for applying a reciprocating linear force to the slip plate for vibrating the slip plate during use. Although the invention is illustrated with respect to an actuator having a pair of pistons for producing output forces in opposite directions, this is one embodiment of the invention; the invention also can be adapted for use with a single piston actuator.

The drawings (see FIGS. 2 and 3) illustrate one embodiment of the vibration test fixture, in which the bearings 14 are rigidly affixed to the upper surface of a steel base plate 24, preferably of rectangular configuration. An upright outer wall 26 extends around the rectangular outer perimeter of the base plate to provide a means for retaining lubricating oil within the fixture. A manifold (not shown) mounted to one edge of the base plate provides for filtration and recirculation of lubricating oil through the bearings.

The bearings 14 at opposite ends of the drive actuator unit preferably comprise separate three-layer structures, which are shown in more detail in U.S. Pat. No. 4,996,881. Each bearing has a generally rectangular bottom plate; a pair of laterally spaced-apart, long and narrow, generally rectangular middle plates extending parallel to each other along opposite sides of the bottom plate; and a pair of laterally spaced apart, generally rectangular top plates extending parallel to each other along opposite sides of the middle plates. The narrow middle plates form a wide, shallow bottom portion of an inverted T-shaped channel 28 extending along the central axis of each bearing. The top plates are wider than the middle plates, and are spaced apart by a narrow gap 30 which forms the narrow portion of the inverted T-shaped channel in each bearing. The inverted T-shaped channels are aligned along a common drive axis of the fixture. The flat upper bearing surfaces 12 are formed at the tops of the top plates and lie in a common flat plane to provide bearing support for the bottom of the slip plate 10. A rectangular top surface 32 of the actuator drive unit 16 is aligned in a common flat plane with the upper surfaces 12 of the bearings 14 to provide a continuous flat supporting surface for the slip plate.

The slip plate is mounted for guided single axis travel relative to the bearings by separate inverted T-shaped guide members 34 rigidly affixed to the bottom of the slip plate. These inverted T-shaped guide members are slidably engaged in corresponding inverted T-shaped channels 28 in the bearings 14 for guiding the slip plate 10 during use. Each guide member 34 is a two-component structure which includes a relatively wider lower guide member bearing block 36 that slides in the wide bottom portion of the T-shaped channel, and a relatively narrower upper guide member bearing block 38 of rectangular configuration which slides in the narrow upper portion 30 of the T-shaped channel. Each upper bearing block is affixed to a corresponding lower bearing block and is also rigidly affixed to the bottom of the slip plate. Threaded holes 40 in each bearing guide member 34 and cooperating threaded holes 42 in the slip plate receive fasteners for rigidly affixing the bearing guide members to the slip plate. The bearing guides 34 provide means for guiding single-axis travel of the slip plate along the inverted T-shaped channels 28 in the bearings.

Oil flow ports 44 open through the working faces of each bearing block and the T-shaped channel in each bearing block. This provides a means for supplying a film of lubricating oil to the lateral and vertical restraint surfaces of the bearing for lubricating travel of the T-shaped guide member 34 relative to the channel 28 in each bearing, together with means for supplying a film of lubricating oil to the upper bearing surface 12 for lubricating reciprocating longitudinal travel of the slip plate 10 on the bearing surfaces.

The hydraulic servo valve 18 and double-acting pistons 20 and 22 are contained in a modular unit integrated into the slip table bearing system, by mounting the actuator module 16 in-line between the bearings 14 that guide and support the slip plate 10. The pistons 20 and 22 contained in the hydraulic valve actuator reciprocate on a common axis 45 (see FIG. 1) and extend outwardly from opposite sides of the actuator housing 46. The pistons are aligned and engaged with the T-shaped bearing guide members 34 so that reciprocating travel induced in the actuator pistons causes alternating thrust forces from the pistons to drive the bearing guide members in a corresponding reciprocating motion along the bearing guide axis of travel. The hydraulic servo valve 18 controls piston movement by providing a controllable frequency input for inducing vibration motion directly to the pistons. The servo valve unit 18 contains a transducer such as a voice coil unit 47 connected directly to a pilot valve 48 (shown best in FIGS. 5 and 6) for driving the pilot valve at controllable frequencies set by an electronic voice coil drive input signal 49 (see FIG. 6). The pilot valve motion produces hydraulic fluid flow control outputs $C_1$ and $C_2$ (see FIG. 5) at the controlled frequency from the servo valve. The fluid control outputs from the servo valve are directed toward the faces of the pistons 20 and 22 to vibrate the pistons at the frequency set by the input signal 49. The hydraulic servo valve 18, the double-acting piston actuator, and the voice coil drive unit 47 are all integrated into a common module 16 that is directly integrated into the slip plate bearing guide system and positioned beneath the center of the slip table. This avoids the prior art use of external drive means, such as electrodynamic actuators, or an external single axis hydrostatic bearing actuator drive common in prior art hydraulic slip tables. Other improvements are also provided as described in more detail below.

Figure 2:
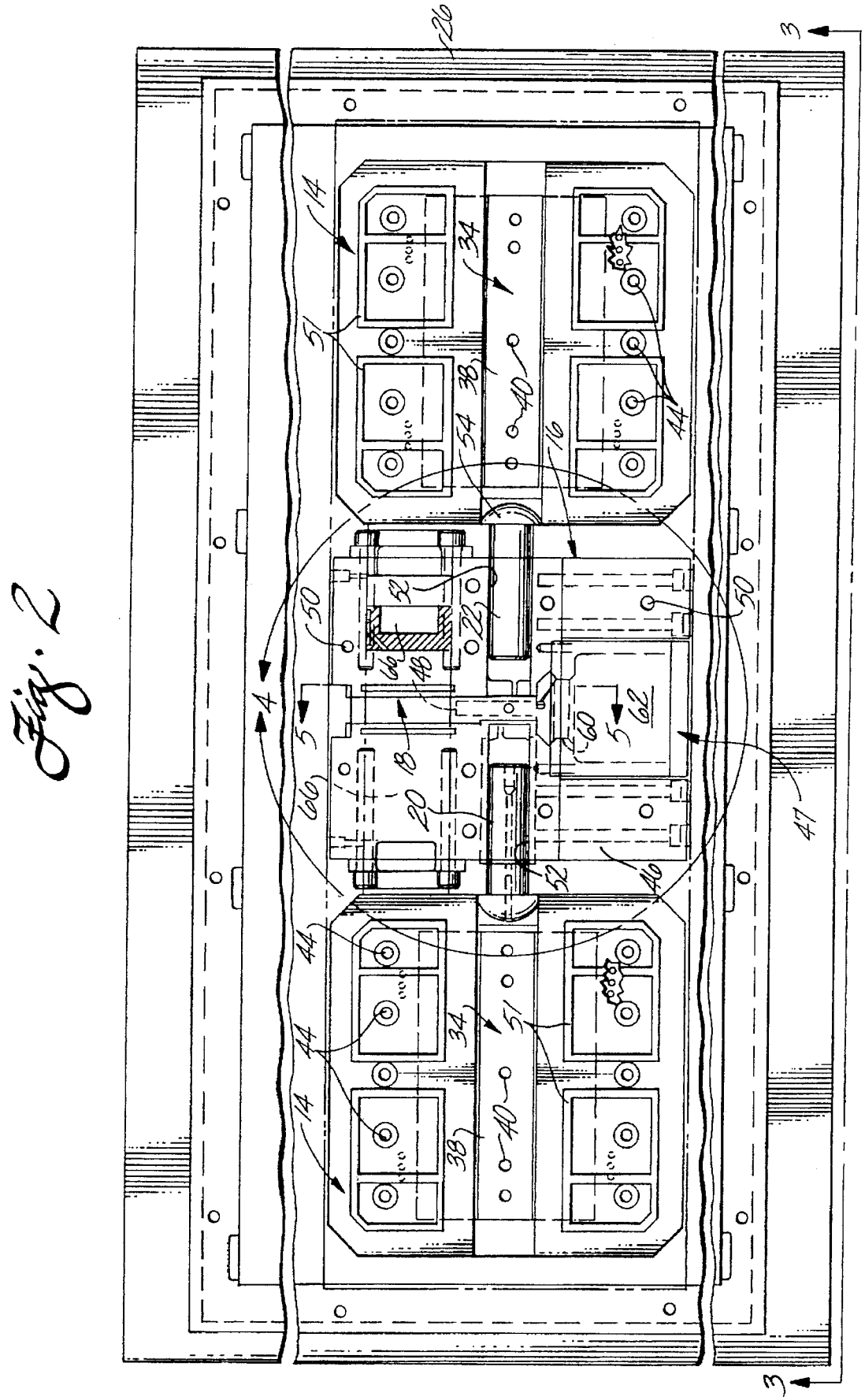
FIG. 2 is a fragmentary plan view showing a hydraulic servo valve and double-acting piston actuator integrated into the test fixture between a pair of spaced-apart bearings that support a vibration table.
Figure 3:
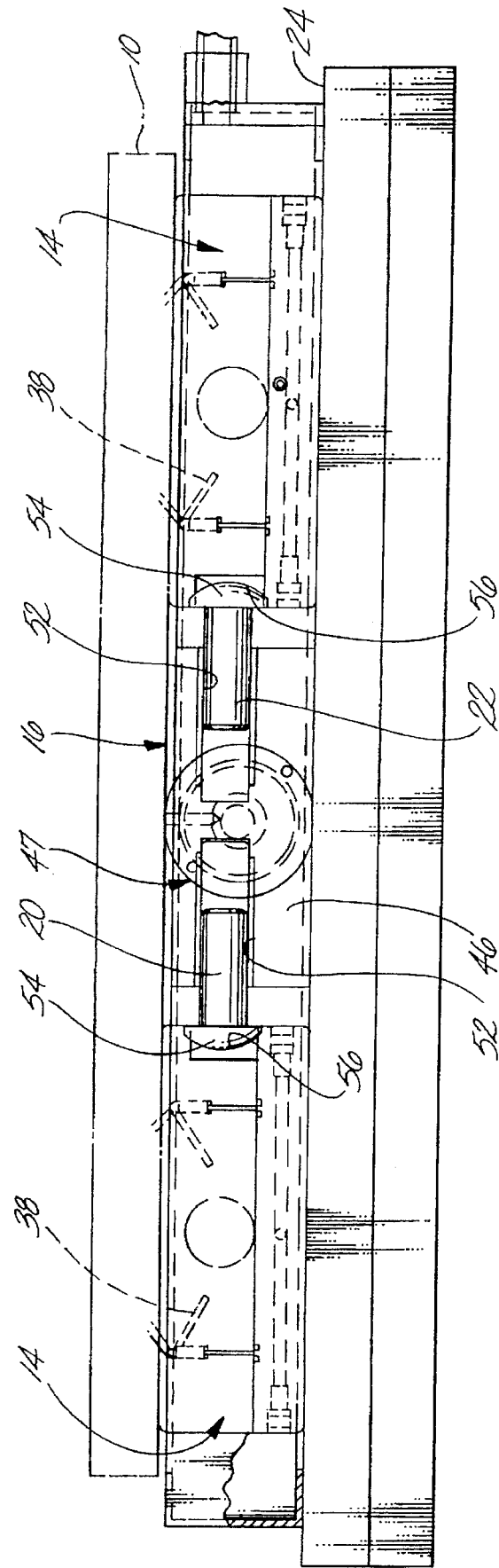
FIG. 3 is a side elevation view taken on line 3—3 of FIG. 2.

FIGS. 2 and 3 show the integrated servo valve and double-acting piston actuator module 16 mounted to the base plate 24 of the test fixture between the spaced-apart pair of T-shaped bearing guide members 34 aligned on the axis of vibration 45. The outer housing 46 of the actuator is mounted in-line between the T-shaped bearings 14 that support opposite sides of the slip plate. As mentioned previously, the actuator housing 46 has a flat rectangular top surface 32 at the same elevation as the flat rectangular top surfaces 12 of the bearings 14, to provide a continuous, flat top surface for supporting the load of the reciprocating slip plate 10. The actuator housing 46 includes ports 50 for supplying low pressure lubricating oil to the top surface of the housing to provide a lubricating film for the undersurface portion of the slip plate that rests on top of the actuator housing.

The pistons 20 and 22 are aligned along the common axis of vibration 45, and opposite end portions of the pistons project outwardly from opposite sides of the actuator housing 46. The pistons each reciprocate in corresponding cylinders 52 contained internally within the actuator housing. The outer end portions of the pistons have spherically curved thrust-applying bearings 54 that apply pressure to matching recessed spherically curved bearing surfaces of piston guide cups 56 affixed to corresponding T-shaped bearing guide members 34 aligned with the axes of the pistons. The hydraulic fluid pressure within the system causes the spherical ends of the piston bearings to apply pressure to the spherical bearing cups 56. The spherical ends of the pistons are otherwise free to slide or rotate relative to the spherical bearing cups, which provides a self-alignment function for the pistons. The pistons are shown as uniform diameter members with enlarged spherical bearings at the ends; alternatively, the pistons can have reduced diameter piston rods projecting from opposite ends of the actuator housing with separate enlarged spherical bearings 54 at the ends of the piston rods.

Figure 4:
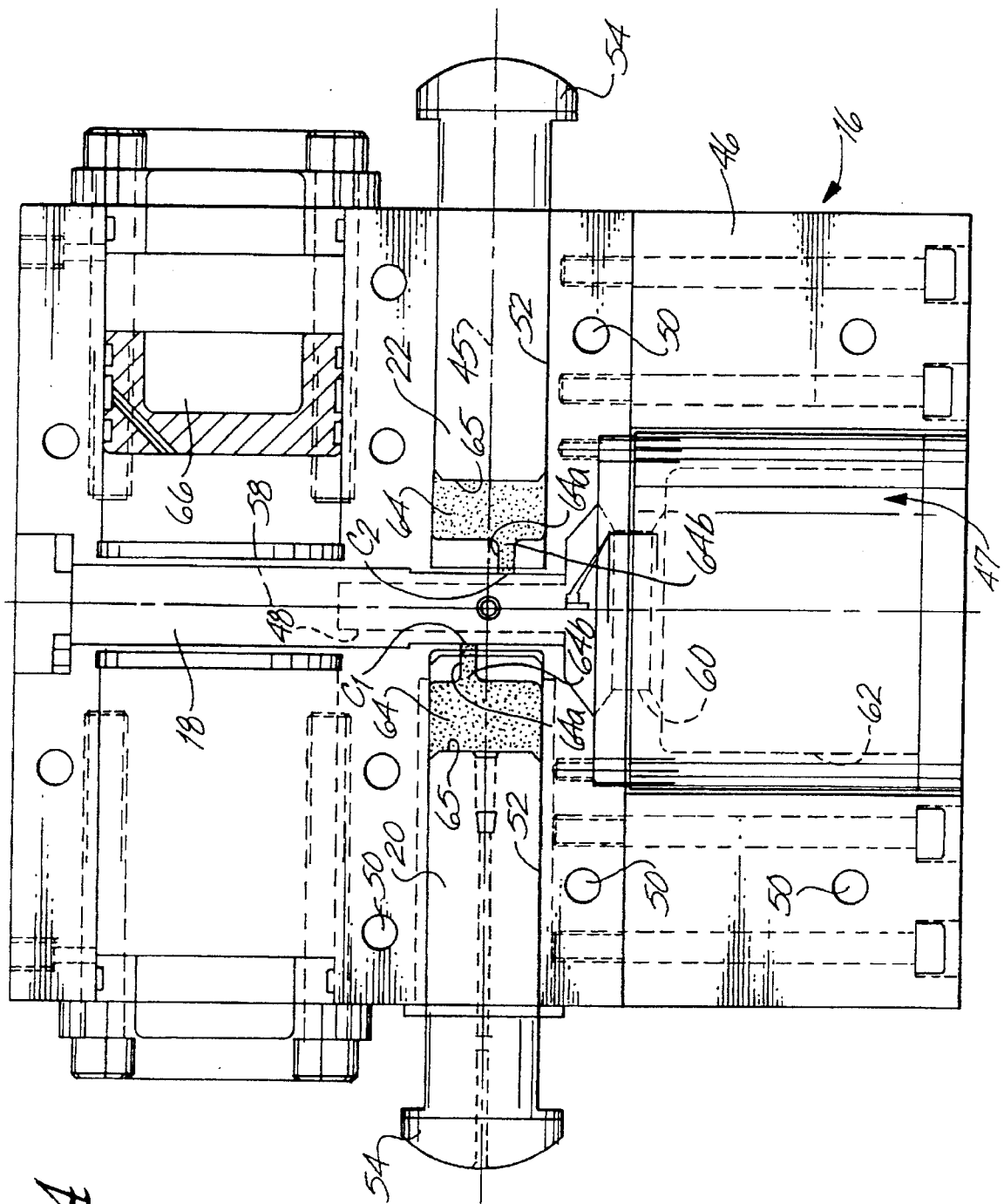
FIG. 4 is an enlarged top plan view of the apparatus shown within the circle 4 of FIG. 2.

FIGS. 2 through 4 best illustrate the hydraulic servo valve assembly 18 incorporated into the piston actuator housing 46. The servo valve assembly, described in more detail below, includes the pilot valve spool 48 (see also FIG. 6)

which is contained within the servo valve unit 16 and mounted within the actuator housing 46 along an axis 58 perpendicular to the piston axis of travel 45. The pilot valve spool 48 is driven at controllable frequencies by a voice coil 60 contained within the voice coil unit 47. An electromagnetic field 62 for the voice coil is also contained within the voice coil unit 47 adjacent the voice coil 60. The electronically controlled drive input signal 49 (see FIG. 6) to electromagnetic field coil 62 induces mechanical vibrational motion in the voice coil. The pilot valve spool 48 of the servo valve assembly 18 is directly connected to the voice coil output, and oscillating motion induced in the voice coil is transmitted directly to the pilot valve spool for reciprocating the pilot valve spool at the same frequency. Vibration of the pilot valve is along the axis 58 perpendicular to the piston axis of vibration. The input drive signal 49 can be a sinusoidal input, a random motion input signal, or it can duplicate measured real-time waveforms. The voice coil represents an example of a transducer which oscillates in response to an alternating current in a magnetic field to generate a vibration motion of the pilot valve along its axis; other similar transducers could be used for the same purpose.

As the pilot valve reciprocates along the axis 58 perpendicular to the piston axis of travel 45, the servo valve unit 18 produces resulting hydraulic fluid flow control outputs $C_1$ and $C_2$ which flow directly into low volume hydraulic fluid pressure chambers 64. The chambers 64 extend from the control outputs of the servo valve to the end faces of the pistons 20 and 22 in the cylinders 52. The resultant forces of the hydraulic fluid flow control outputs $C_1$ and $C_2$ (see FIG. 5) are directed outwardly from the servo valve output ports along axes parallel to the drive axis of the slip table (and perpendicular to the end faces of the pistons); the alternating fluid flow outputs from the servo valve apply these thrust forces to the ends of the pistons at the same frequency as the frequency induced in the pilot valve spool 48 by the voice coil 60. In one embodiment, voice coil input drive signals above about 1,000 Hz and as high as about 2,000 Hz generate corresponding hydraulic fluid flow control outputs directed at the pistons at the same frequency to vibrate the test fixture slip plate at the same frequency level. The low volume hydraulic fluid chambers 64 are shown exaggerated in size in FIG. 4. The passages 64a from the servo valve outlets (at $C_1$ and $C_2$) to the cylinder inlet ports 64b are also exaggerated in size for clarity. The high frequency response of the piston actuator is achieved primarily because the system is designed to minimize as much as possible the volume of trapped compressible hydraulic fluid between the outlet ports $C_1$ and $C_2$ of the servo valve and the end faces 65 of the pistons 20 and 22 which are exposed to the volume of hydraulic fluid contained in the bore of each cylinder. To minimize the volume of trapped fluid, the force-applying ends of the pistons extend outwardly in opposite directions from the piston actuator housing, and the end faces 65 of the pistons, which are opposite from the force-applying ends of the pistons, are positioned adjacent to one another and are exposed to the separate control chambers 64 of hydraulic fluid which are in direct internal communication with the outlet ports of the servo valve. In the preferred embodiment, the servo valve is positioned directly between and in close proximity to the control chambers 64 so that fluid flow control outputs from the servo valve are passed directly into the low volume control chambers 64, while minimizing the total volume of compressible hydraulic fluid between the valve and piston. The invention avoids long and narrow passages or conduits for hydraulic fluid flow between the servo valve and the bore of the piston cylinders. Hydraulic fluid is a compressible substance, and its compressibility in such long, narrow passageways can greatly reduce the high frequency response of the actuator. By minimizing the trapped volume of fluid, which is the main compliant element in the system, the actuator achieves high frequency response.

More specifically, the servo valve outlets are in close proximity to the inlet ports of the cylinders, and the trapped volume of fluid between piston end faces 64 and servo valve outlets $C_1$ or $C_2$ is minimized as much as possible. The fluid flow from the valve to the piston is therefore as direct as possible; the length of each passage 64a is as short as possible, and is preferably of essentially negligible length. The volume of fluid within the cylinder adjacent the piston also is as low as possible, while maintaining sufficient fluid pressure on substantially the entire end face area of the piston. In one embodiment in which the pistons have a diameter of about two inches, the volume of fluid within each cylinder (adjacent the piston end face 65) occupies from nearly zero to about two inches of stroke length, or an average of about one inch. Actual stroke length of the piston operating at high frequencies over about 1000 Hz is about 0.1 inch. The length of the passage 64a is less than about one inch, i.e., less than the radius of the piston, more preferably a fraction of an inch, and as a practical matter is as short as possible.

FIG. 5 is a cross section of the hydraulic servo valve assembly 16 which includes the voice coil 60 rigidly affixed to one end of the pilot valve spool 48 which extends along the center line of the servo valve housing. As mentioned previously, the pilot valve spool 48 reciprocates linearly along the longitudinal axis 58 of the servo valve assembly directly in response to corresponding vibration of the voice coil. The pilot valve ports to a hydraulic pressure supply contained in separate hydraulic accumulators 66 contained in the actuator housing on opposite sides of the servo valve assembly. The hydraulic fluid for producing the servo valve outputs circulates in a closed hydraulic fluid system that ports in and out of the servo valve to and from the hydraulic accumulators. The servo-valve is a four-way valve assembly in which the pilot valve spool is concentrically mounted for reciprocating sliding movement in an elongated cylindrical bore 68 inside a stationary pilot valve sleeve 70. Coil springs 72 apply a spring biasing forces to the ends of the moving pilot valve spool. Hydraulic fluid at pressure $P_{in}$ passes through input ports in the pilot valve spool and along a small diameter concentric bore in the pilot valve spool. The fluid at a pressure $P_{out}$ flows out from pressure output ports near the opposite end of the bore through the pilot valve spool. Sections 78 of reduced diameter adjacent opposite outer ends of the flow edges provide the inlet and outlet openings of the inlet and outlet ports. A reduced diameter central portion 80 of the pilot valve spool between the flow edges 78 opens into a pilot valve hydraulic fluid supply return chamber. The flow edges of the pilot valve spool communicate with cylindrical recessed areas 82 inside the pilot valve sleeve for controlling the cycling and direction of hydraulic fluid pressure control outputs $C_1$ and $C_2$ of the servo valve.

The servo valve assembly also includes a slave stage that provides power amplification for the servo valve. The slave stage includes a movable slave valve spool 84 (also shown in FIG. 7) concentric with the servo valve axis 58 and disposed concentrically around the outside of the pilot valve sleeve 70. The slave stage also includes a stationary slave valve sleeve 86 concentric with and extending around the exterior of the slave valve spool. The slave valve spool has an internal axial bore 88 that slides on a cylindrical outer surface 90 of the stationary pilot valve sleeve 70. The slave valve spool is adapted for spring biased longitudinal reciprocating motion inside the servo valve in response to the alternating hydraulic fluid control pressure outputs induced within the servo valve by the vibrating motion of the pilot valve spool. Such induced motion of the slave valve spool produces the servo valve control pressure outputs $C_1$ and $C_2$ as described in more detail below.

The slave valve spool 84 has longitudinally spaced-apart enlarged cylindrical sections which include first and second end bearings 92 that support sliding travel of the slave valve spool inside a central bore 94 within the stationary slave valve sleeve 86. The ends of the slave valve spool are biased by corresponding coil springs (not shown). First and second cylindrical flow edges 96 are located near the central portion of the slave valve spool. A region 98 of reduced diameter between the flow edges of the slave valve spool opens into a return chamber 100 that communicates with a hydraulic fluid return 102 from the pilot valve. The hydraulic fluid return from the pilot valve to the return section of the slave valve sleeve passes from lateral return ports 104 in the pilot valve sleeve, through communicating lateral return passages 106 extending through the slave valve spool, and through communicating lateral return ports 108 in the slave valve sleeve. These return ports communicate with return ports that lead to the supply section of the slave valve sleeve.

Hydraulic fluid under pressure $P_1$ and $P_2$ is supplied from the return system to the slave valve section through annular passages 110 in the outer housing surrounding the slave valve sleeve 86. Hydraulic fluid under pressure $P_1$ and $P_2$ is supplied to the moving slave valve spool 84 through lateral supply passages 112 extending through the slave valve sleeve to recessed annular supply pressure regions 114 of the slave valve spool adjacent the first and second flow edges 96 of the slave valve spool. Hydraulic fluid under pressure communicates between the flow edges of the slave valve spool and the pressure input ports to the pilot valve through lateral passages 116 extending from the recessed annular region of the slave valve spool, through the body of the slave valve spool and the pilot valve sleeve, and to the pressure input $P_{in}$ of the pilot valve 48.

Alternating hydraulic fluid pressure control outputs $C_1$ and $C_2$ from the servo valve slave stage are produced along spaced-apart recessed annular passages 118 in the outer housing that communicate with corresponding recessed annular control passages 120 in the stationary slave valve sleeve. The hydraulic fluid pressure control outputs $C_1$ and $C_2$ are directed to output stages of the servo valve for direct communication of hydraulic fluid flow from the servo valve to the pistons that are driven in response to fluid flow cycling of the servo valve. Hydraulic fluid under pressure in the recessed pressure regions 120 of the slave valve sleeve communicate with first and second lateral passages in the slave valve sleeve 122 leading to the control output regions $C_1$ and $C_2$ of the servo valve. The alternating flow control outputs $C_1$ and $C_2$ are controlled by the flow edges 96 of the slave valve spool 84 which reciprocates to open and close the supply of hydraulic fluid under pressure to the outputs $C_1$ and $C_2$ of the servo control valve. In the closed hydraulic fluid pressure system, axial cycling of the slave valve spool in response to corresponding cycling of the pilot valve spool alternately opens and closes the control passages 120 to the control output regions of the servo valve. A pressure output from control region at $C_1$ simultaneously produces a reverse flow of control pressure from the control region at $C_2$ to the return path, and vice versa.

During reciprocating motion of the pilot valve, hydraulic pressure acts alternately on differential areas shown at $P_A$ and $P_B$. Hydraulic fluid under pressure reaches pressure area $P_A$ through lateral outlet passages 124 in the pilot valve sleeve and 126 in the slave valve spool. Hydraulic fluid under pressure reaches pressure area $P_B$ through lateral passages 128 in the pilot valve sleeve and 130 in the slave valve spool. The differential pressure at areas $P_A$ and $P_B$ causes cycling of the slave valve at the same frequency as the pilot valve. Axial reciprocating travel of the slave valve alternately opens and closes the lateral control passages 120 in the slave valve sleeve to receive or to block off hydraulic fluid pressure in the lateral pressure passages. This causes hydraulic fluid flow at control outputs $C_1$ and $C_2$ to cycle at the frequency input from the voice coil to the pilot valve; and these control outputs are directed to the end faces of the pistons in a low volume hydraulic fluid pressure circuit that cycles the pistons at the frequency produced by control outputs $C_1$ and $C_2$.

Thus, vibrating longitudinal single-axis motion induced in the pilot valve by the voice coil causes hydraulic fluid under pressure to flow as control outputs in a closed hydraulic fluid system in which the control outputs are alternately directed to the pistons 20 and 22 in small, short, low volume pulses at the same frequency as the motion induced by the voice coil. In addition, the slave valve stage of the servo valve is concentric with the pilot valve stage. This arrangement avoids long narrow, passages or lines between separate pilot valve and servo valves characteristic of the prior art. This minimizes the compliancy effects of hydraulic fluid between the input stage of the servo valve and its output. By minimizing the compliancy of the hydraulic fluid contained in the servo valve, better high frequency response is achieved. The large size (area) of the servo valve slave stage spool also increases valve flow rate substantially. This increased valve flow combines with the reduced compliancy (of the trapped compressible fluid) to achieve vibration response at high frequencies. The concentric arrangement of the pilot stage and the slave stage also provides a much smaller servo valve unit which can be incorporated effectively into the piston actuator housing so that both outputs from the servo valve are from opposite sides of the servo valve and directly into the low volume fluid control chambers adjacent the end faces of the pistons.

The hydraulic vibration test fixture has the following advantages. The actuator pistons drive the moving elements of the bearings both in front of and behind the actuator instead of at the edge of the slip plate. The single actuator thus inputs its force to the slip plate through the two slip plate/T-film bearing connections, spreading the force input over a large area. Multiple small hydraulic shakers can be used to simultaneously provide high frequency response and input the vibration force uniformly to the entire table surface. The shakers are modular, including both the servo valve and piston in a single body. The shaker can be mounted in a common sump and has no oil seals. The oil is allowed to escape from the actuator assembly and can be collected in the sump. The sump can be sealed so that contaminants cannot get in or out. In the case of the horizontal vibration table system shown in the drawings, in which the shaker is used in conjunction with the T-bearings, the actuator is configured to fit the T-film bearing envelope so that it can replace the bearing in a T-film table assembly directly. The top surface of the actuator has an oil film bearing similar to the T-film bearing to lubricate and support the slip plate. The shaker shafts provide lateral motion restraint and the spherical couplings allow the shakers to go out of phase without damage. The double piston design ensures a preloaded load path, eliminating backlash, and it allows the valve assembly to be mounted between the pistons with extremely short oil passages from the valve to the pistons. This enhances the high frequency response of the actuator system. The hydraulic accumulators are integral with the shaker body. All oil porting is internal and are no external oil lines. The pistons drive the table or T-bearing elements through spherical pad bearings. This has the benefits of the actuator driving either a single axis table or a multiple degree of freedom table. It also eliminates alignment as a critical parameter during assembly. The integrated shaker uses the high power-to-size ratio of hydraulic shakers and can produce vibration above 1,000 Hz and up to 2,000 Hz at high acceleration levels. In one embodiment the actuator produces 3,500 pounds of force rms for a random signal input from 20 to 2,000 Hz. Higher force levels can be produced with multiple actuator modules aligned to apply the force in a common direction.

EXAMPLE

The dynamic performance of an electro-hydraulic servo system may be quantified with respect to three parameters: hydraulic natural frequency, required hydraulic flow rate, and freedom from non-linearities. All of these factors are strongly affected by the distance between the servo valve and the actuator piston. It may be shown that performance is greatly enhanced by making this distance as short as possible.

To illustrate this point quantitatively, consider the following two split actuator systems. The first is a prior art design illustrated in FIG. 8, in which the two half actuators bear on opposite sides of a projection from the shake table, with the servo valve located at the center and connected by pipes or hoses to the far ends of the actuators. The second system, the subject of this invention, has the two actuators placed back to back, with the servo valve connected to the pistons by passages of negligible length.

Assume that the pistons are 2 inches in diameter, with a maximum stroke of ±0.5 inches. The system has peak velocity of 50 inches/second and a peak pressure of 3,000 psi. The displacement and velocity correspond to those commonly achieved by conventional electrodynamic shakers. Assume further, that the fluid velocity in the lines is limited to 150 inches/seconds, thus requiring a cross sectional area of ⅓ square inches. Finally, assume that the distance between the cylinder end and the servo valve outlet in the first case is 12 inches, and in the second case essentially zero.

The first parameter, the hydraulic stiffness of the actuator is:

$$K = \frac{4A^2B}{As + V'}$$

where:

K=spring rate,
A=piston area,
B=fluid bulk modulus,
s=stroke, and
V'=volume in the connecting lines.

For the first actuator, the effectie bulk modulus, including line and cylinder compliance, is found to be about 100,000 psi. Thus, $$K1 = \frac{4\pi^2(100,000)}{\pi + 24/3} = 354,000 \text{ inch-pounds}$$

For the second case, the effective bulk modulus is about 200,000 psi, so K2=2,500,000, or a factor of more than seven times greater. Since Natural Frequency is proportional to the square root of the stiffness, the new system will have more than 2.6 times the natural frequency of the old system and may thus be presumed to be controllable within a higher frequency range.

For example, assume that the moving mass is 300 pounds, so that the peak acceleration is about 31 G, a performance achievable by a good electrodynamic shaker. The hydraulic natural frequency of the new shaker will be about 280 Hz, while it is only 107 Hz for the old one.

The second parameter, the required flow rate, is determined as follows. It is common practice to drive electrohydraulic shakers to frequencies much higher than their natural frequency in order to do effective vibration testing. However, a limit to the high frequency performance is set by the compressibility of the flow, that is, the extra flow required to compress the fluid if the piston is held stationary. The compressible flow becomes the dominant flow at high frequencies (above the natural frequency) where the piston motion is essentially zero.

The compressible flow is:

$$Q_c = VPF/B$$

where:

V is the total trapped volume,
P is the peak pressure, and
f is the sinusoidal excitation frequency.

The volumes of the new and old configurations are ($\pi$) and ($\pi$+8) or 3.14 and 11.14 cubic inches, respectively. The compressible flows at 1,000 Hz then are 47.1 and 334 cubic inches per second (cis) respectively. (Assuming the same effective bulk moduli as before.) The old design requires seven times the flow of the new design, and therefore a valve capable of flowing seven times as much oil. An "avalanche effect" comes into play as the larger servo valve itself has lower frequency response and the greater flow requires larger passages, which, in turn, add to the compressible flow requirement. Thus, the possibility of reaching high frequencies diminishes with every increment of added volume between the servo valve and the actuator. This is avoided in the new design and is fundamental to its higher frequency response.

The third parameter of performance, the system nonlinearity, is related directly to the distance between the valve and the pistons (as opposed to the volume between them). Because of the finite velocity of sound in the fluid, a pressure pulse originating at the servo valve will travel to the actuator and back to the valve in a finite time. A series of such pulses making up a sinusoidal excitation will excite a frequency of:

$$f = Vs'/2$$

where:

V is the velocity of sound, about 35,000 to 50,000 inches/second, and
s' is the distance between valve and the piston.

For the old system, with s'=12 inches, this results in an apparent frequency of about 1,500 Hz. This standing pressure wave shows up as noise in the acceleration of the actuator (and therefore on the test specimen). In the new system, with s'=1 inch, the pressure pulse frequency is about 17,500 Hz. No standing waves or extraneous noise will be produced in the frequency range normally of interest in mechanical vibration testing.

Figure 9:
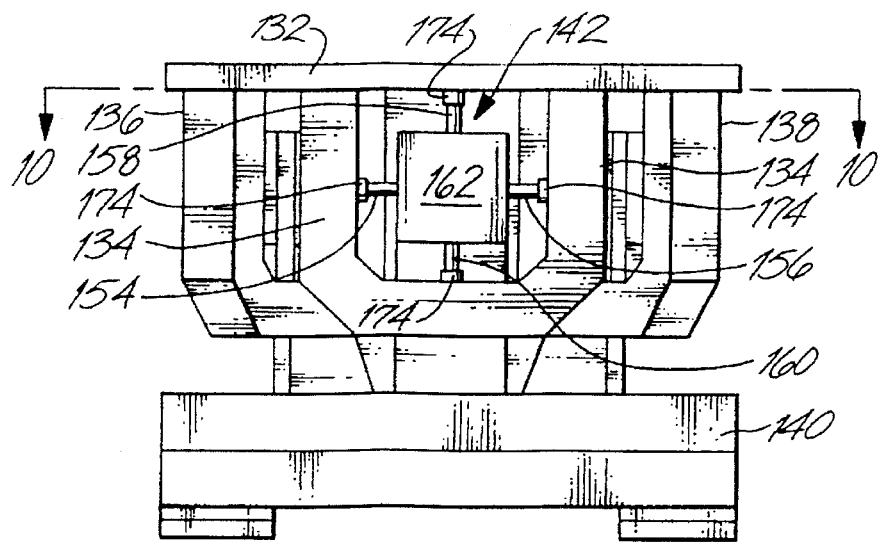
FIG. 9 is a semi-schematic front elevation view showing one embodiment of a multiple-axis, multiple degree-of-freedom vibration test fixture.
Figure 10:
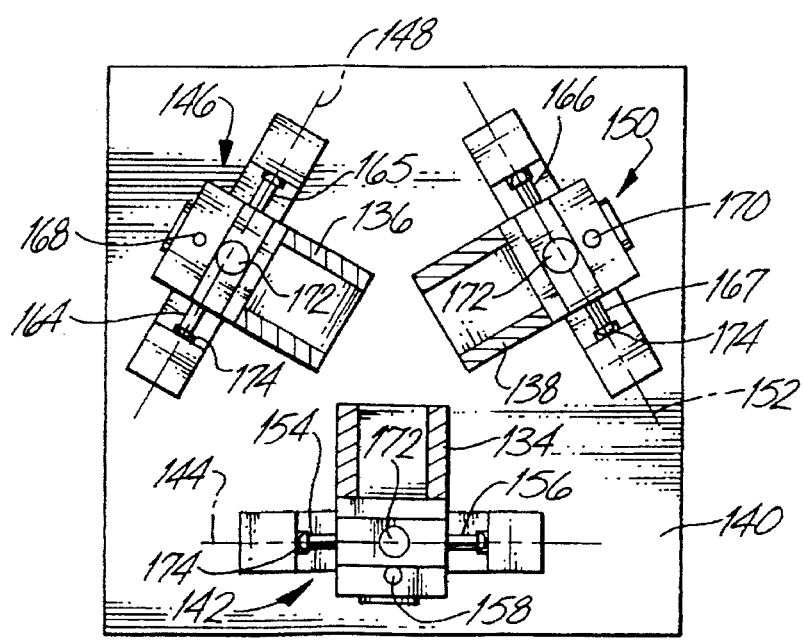
FIG. 10 is a semi-schematic top view taken on line 10—10 of FIG. 9.

FIGS. 9 and 10 schematically illustrate an alternative form of the invention comprising a multiple-axis, multiple degree-of-freedom vibration test fixture 130. The fixture includes a normally horizontal upper fixture base 132 for carrying a unit under test. The base 132 is supported by three sets of upwardly extending pairs of rigid support arms 134, 136 and 138 aligned at separate angular orientations around the bottom of the upper base 132. The support arms are mounted to a rigid stationary lower base 140 so as to accommodate vibration motion of the upper base of the fixture in both the vertical plane and the horizontal plane. A separate piston actuator module is affixed to each support arm system. Each piston actuator module is aligned on an axis extending at an angle with respect to the axis of the other two modules. Thus, as shown best in FIG. 10, a first module 142 is aligned along an axis 144, a second module 146 is aligned along an axis 148 and a third module 150 is aligned along an axis 152. Each module includes a pair of piston actuators combined as a unit in a separate housing, with one set of pistons reciprocating along a horizontal axis and a second set of pistons reciprocating along a vertical axis. FIG. 9 best shows the first module 142 having horizontal piston actuators 154 and 156 and vertical piston actuators 158 and 160 extending outside a common housing 162 along mutually orthogonal axes. FIG. 10 shows the horizontal piston actuator pairs for each of the three modules, including piston actuators 164 and 165 for module 146 and piston actuators 166 and 167 for piston actuator module 150. Vertical piston actuators are shown in FIG. 10, and these include the piston 158 of the first module 142, a vertical piston 168 for module 146 and a vertical piston 170 for module 150.

Each of the three modules preferably comprises a hydraulic servo valve controlled-double acting piston actuator similar to the servo valve-piston actuator shown in FIGS. 1 through 7. Thus, each unit includes a separate voice coil (shown schematically at 172 in FIG. 10) for providing an oscillating input signal to each servo valve of each piston actuator module. There are two voice coil operated hydraulic servo valves for each unit, one for the horizonal pair of pistons and one for the vertical pair of pistons. The hydraulic servo valve and voice coil controllers for each module are preferably the concentric pilot valve-slave valve arrangement similar to that shown in FIG. 5.

The outer working ends of the four piston rods extending to the outside of each housing of each module are engaged with rigid portions of the fixture support system. Thus, referring to FIG. 9, the ends of the horizontal pistons 154 and 156 are engaged with opposite support arms 134, the end of the vertical piston 158 is engaged with the bottom of the rigid upper support base 132, and the end of the vertical piston 60 is engaged with the bottom of the u-shaped structure which includes the upright support arms 134. The ends of the piston rods in the other modules 146 and 150 are similarly affixed to the fixture support system. In each module the connections between the ends of the pistons and the fixture support system is through a cooperating pair of spherical bearings similar to the spherical bearing connections illustrated in FIGS. 1 through 4. These spherical bearing connections are illustrated schematically at 174 in FIGS. 9 and 10. In each spherical bearing connection the hydraulic servo system applies fluid pressure outwardly on the piston arms to hold them in pressure contact with their cooperating support bearings. Thus, the spherically curved bearing ends of the piston rods are able to slide and rotate relative to their corresponding spherical bearing connections to the fixture support system. As a result, vibrational forces acting along any of the three axes of the vibration modules are decoupled from motion induced on them from vibration forces induced on the fixture from vibration of either or both of the other two vibration modules.

During use of the vibration fixtures shown in FIGS. 9 and 10, the piston actuator pairs in each module are actuated to oscillate along their respective axes in accordance with any desired waveform test signal. This permits the vibration table to be vibrated along orthogonal x and y-axes and rotated with a z-axis rotation in the horizontal plane by corresponding combinations of vibration of the three sets of horizontal piston actuators. Separately, components of vertical forces are induced by the three sets of vertical piston actuators to oscillate the table in various combinations of pitch, yaw or heave orientations in the vertical plane, combined with horizontal plane movement. This provides a multiple-axis, multiple degree-of-freedom vibration test fixture.

Figure 14:
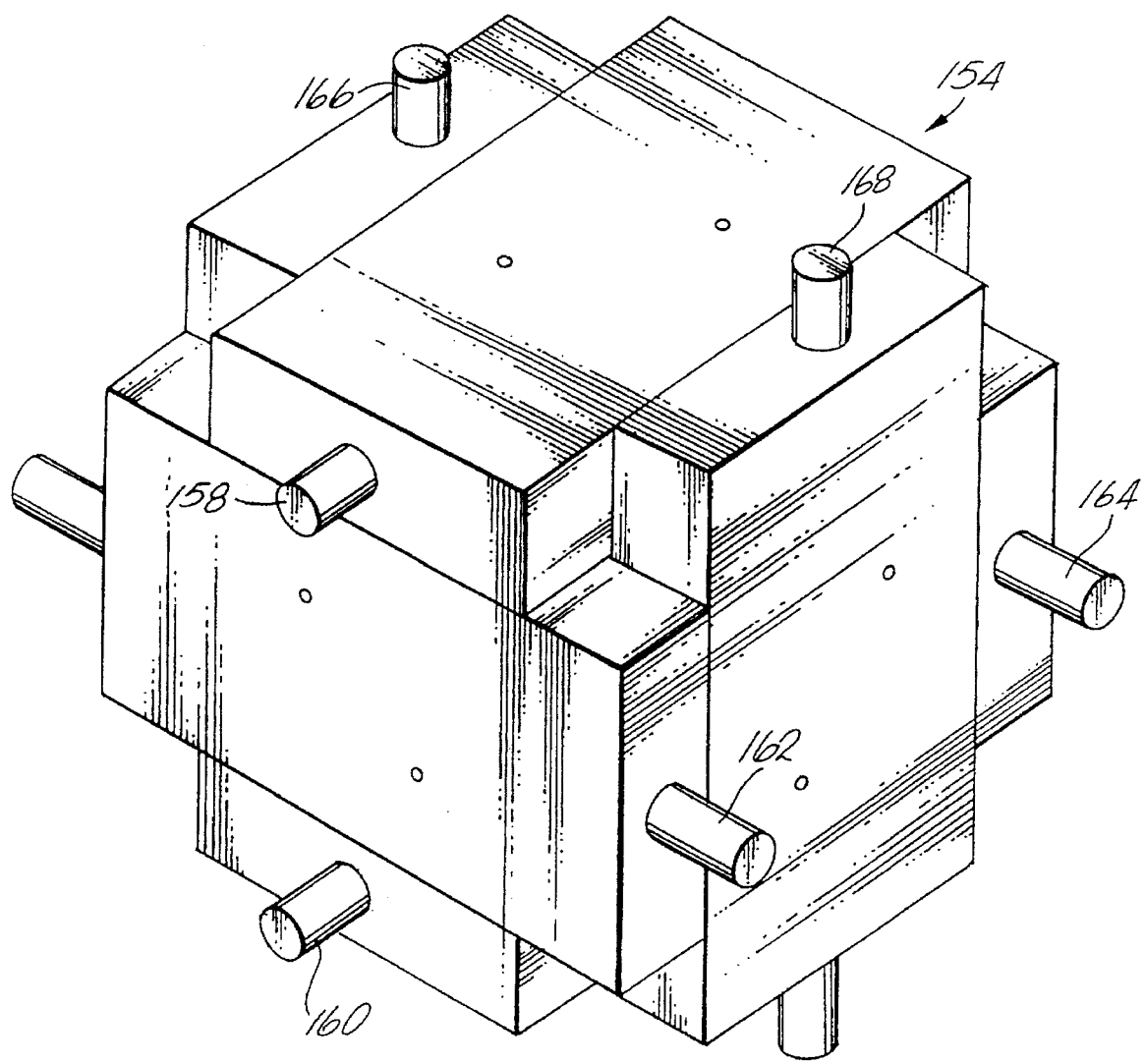
FIG. 14 is a semi-schematic perspective view of a multiple-axis drive system of the test module shown in FIGS. 11–13.

FIGS. 11 through 14 illustrate an alternate form of the invention comprising a multiple-axis, multiple-degree-of freedom vibration test fixture 150 which includes a cube shaped rigid outer fixture 152 having end faces in six mutually orthogonal planes. Separate units under test can be affixed to the cube fixture base on any of the five exposed end faces for vibrational testing as desired. The cube fixture is actuated by a hydraulic servo valve-controlled multiple piston actuator 154 contained within the interior of the cube fixture. The multiple piston actuator is best shown in FIG. 14. This piston actuator includes six separate pairs of piston actuators aligned along six separate axes for inducing vibration motion to the cube fixture base to oscillate the fixture with six degrees of freedom. In the illustrated arrangement, the six pairs of piston actuators are mounted on a common central actuator support 156. The actuators include an upper horizontal piston actuator 158 and a lower horizontal piston actuator pair 160 extending above one another in a common vertical plane; a pair of horizontally extending and laterally spaced-apart piston actuator pairs 162 and 164 on opposite sides of the actuator unit lying in a common horizontal plane; and a pair of laterally spaced-apart upright piston pairs 166 and 168 on opposite sides of the actuator unit extending in a common vertical plane.

Each piston actuator pair is similar to the double-acting piston actuator illustrated in FIGS. 1 through 4, and each is controlled by a separate voice coil-driven concentric servo valve unit similar to that shown in FIGS. 5 through 7.

Further, the piston actuators of each actuator pair have corresponding spherical bearing connections similar to those described above and illustrated schematically at 170. As mentioned previously, these spherical bearing connections decouple the vibrational motion of each actuator pair unit from the motion induced on the fixture in other directions by simultaneous operation of the other vibration test fixtures. Thus, the vibration test fixture can be vibrated in multiple axes with multiple degrees of freedom.

What is claimed is:

1. A high frequency linear hydraulic servo valve-actuated vibration test assembly for producing alternating hydraulic fluid flow control outputs the servo valve-actuated test assembly comprising:

an energy input source comprising a transducer to receive an alternating input signal of a selected frequency and convert the input signal to linear mechanical vibrational motion;

a servo valve having a pair of fluid flow control output ports and in which an output flow of hydraulic fluid is produced from the control output ports of the servo valve; the servo valve including a movable hydraulic pilot valve spool that receives the vibrational motion from the transducer to apply linear reciprocating motion to the pilot valve spool along an axis; a movable hydraulic slave valve spool surrounding and concentric with the pilot valve spool; a fixed pilot valve sleeve surrounding and concentric with the pilot valve spool, the pilot valve sleeve located between the pilot valve spool and the slave valve spool, to direct alternating fluid flow to the slave valve spool as a result of the linear motion of the pilot valve spool to thereby induce linear motion of the slave valve spool; and a fixed slave valve sleeve surrounding and concentric with the slave valve spool to receive alternating fluid flow from the movable slave valve spool to direct the output flow of hydraulic fluid to the fluid flow control output ports of the servo valve, the slave valve spool and the slave valve sleeve providing a power amplification stage for the servo valve output flow that minimizes the volume of trapped hydraulic fluid passing from the pilot valve spool and the pilot valve sleeve to the output ports of the servo valve;

the servo valve-actuated test assembly further comprising a vibration test fixture having a slip table and a piston actuator affixed to the slip table, the output flow of hydraulic fluid from the control output ports of the servo valve directed to the piston for applying a reciprocating linear motion to the piston; and in which the output flow from the control outlet ports of the servo valve has an output frequency and the reciprocating motion of the piston is transferred to the slip table to induce vibrational motion in the slip table at a frequency corresponding to the output frequency of the output flow of fluid from the servo valve.

2. Apparatus according to claim 1 in which the energy input to the servo valve comprises a voice coil for a applying reciprocating linear motion to the pilot valve spool at controlled frequencies, including means for producing alternating output flow from the control output ports of the servo valve in response to the linear reciprocating motion of the pilot spool.

3. Apparatus according to claim in which the slip table is vibrated at frequencies in the range from about 1000 Hz. to about 2000 Hz.

4. A high frequency linear hydraulic servo valve-actuated vibrating test assembly for producing alternating hydraulic fluid flow control outputs the servo valve-actuated test assembly comprising:

an energy input source comprising a transducer to receive an alternating input signal of a selected frequency and convert the input signal to linear mechanical vibrational motion;

a servo valve having a pair of fluid flow control output ports and in which an output flow of hydraulic fluid is produced from the control output ports of the servo valve; the servo valve including a movable hydraulic pilot valve spool that receives the vibrational motion from the transducer to apply linear reciprocating motion to the pilot valve spool along an axis; a movable hydraulic slave valve spool surrounding and concentric with the pilot valve spool; a fixed pilot valve sleeve surrounding and concentric with the pilot valve spool, the pilot valve sleeve located between the pilot valve spool and the slave valve spool, to direct alternating fluid flow to the slave valve spool as a result of the linear motion of the pilot valve spool to thereby induce linear motion of the slave valve spool; and a fixed slave valve sleeve surrounding and concentric with the slave valve spool to receive alternating fluid flow from the movable slave valve spool to direct the output flow of hydraulic fluid to the fluid flow control output ports of the servo valve, the slave valve spool and the slave valve sleeve providing a power amplification stage for the servo valve output flow that minimizes the volume of trapped hydraulic fluid passing from the pilot valve spool and the pilot valve sleeve to the output ports of the servo valve;

the servo valve-actuated test assembly further comprising a vibration test fixture having a fixture base for carrying a unit under test, and a hydraulic vibration actuator affixed to the fixture base and comprising a pair of opposed cylinders, each cylinder having a separate piston that reciprocates along a linear axis in a corresponding bore within the cylinder, each piston having a corresponding piston rod, the piston rods extending in opposite directions from the actuator, each piston having an end face opposite from the piston's corresponding piston rod, said end face exposed to trapped hydraulic fluid contained within a volume in the bore adjacent the end face of each piston, each cylinder having a separate inlet port to the trapped volume of fluid adjacent the piston, and in which the hydraulic servo valve output flow from the control output ports of the servo valve are connected to the inlet ports of the pistons for supplying hydraulic fluid to the trapped volumes within the piston cylinders for reciprocating the piston rods to induce a linear vibrating motion to the fixture base.

5. Apparatus according to claim 4 which the pistons and cylinders are spaced apart and the servo valve is located in a space between the pistons with the control output ports of the servo valve in close proximity to the inlet ports of the cylinders so as to minimize the volume of hydraulic fluid flow from the servo valve to the piston cylinders.

6. Apparatus according to claim 5 in which the vibration test fixture base includes a horizontal slip table, and in which the spaced-apart pistons and the servo valve are affixed to a bottom center portion of the slip table.

7. Apparatus according to claim 6 in which the end face of each piston is in pressure contact against a support affixed to the fixture base, with matching spherically curved bearing surfaces between each piston rod end and corresponding support, to allow for relative sliding and rotating motion between the bearing surfaces.

8. Apparatus according to claim 4 which the energy input to the servo valve comprises a voice color applying reciprocating linear motion to the pilot spool at controlled frequencies, including means for producing alternating output flow from the control output ports of the servo valve in response to the linear reciprocating motion of the pilot spool.

9. Apparatus according to claim 6 in which the slip table is vibrated at frequencies in the range from about 1000 Hz. to about 2000 Hz.

* * * * *

UNITED STATES PATENT AND TRADEMARK OFFICE
CERTIFICATE OF CORRECTION

PATENT NO. : 5,665,919
DATED : September 9, 1997
INVENTOR(S) : William B. Woyski; Robert C. Tauscher; Klaus L. Cappel It is certified that error appears in the above-indentified patent and that said Letters Patent is hereby corrected as shown below:

On the title page, Item [75], the "Inventors:" should read
    William B. Woyski, Anacortes;
    Robert C. Tauscher, Friday Harbor;
    Klaus L. Cappel, Friday Harbor,
    all of Wash.

Column 13, line 65, change "effectie" to -- effective --.
Column 17, line 39, before "applying" delete "a".
Column 17, line 44, after "pilot" insert -- valve --.
Column 17, line 45, after "according to claim" insert -- 1 --.
Column 18, line 38, before "which" insert -- in --.
Column 18, line 54, before "which" insert -- in --.
Column 18, lines 57,60, after "pilot" insert -- valve -- (both occurrences).

Signed and Sealed this

Second Day of June, 1998

Attest:

BRUCE LEHMAN

*Attesting Officer*      *Commissioner of Patents and Trademarks*